United States Patent
Helms et al.

(10) Patent No.: US 10,683,419 B2
(45) Date of Patent: Jun. 16, 2020

(54) REDOX-ACTIVE SUPRAMOLECULAR POLYMER BINDERS DERIVED FROM PERYLENE BISIMIDE NANOWIRES ENABLE HIGH-RATE LITHIUM-SULFUR BATTERIES

(71) Applicants: Brett A. Helms, San Francisco, CA (US); Peter D. Frischmann, Berkeley, CA (US); Yoon Hwa, Emeryville, CA (US); Elton J. Cairns, Walnut Creek, CA (US)

(72) Inventors: Brett A. Helms, San Francisco, CA (US); Peter D. Frischmann, Berkeley, CA (US); Yoon Hwa, Emeryville, CA (US); Elton J. Cairns, Walnut Creek, CA (US)

(73) Assignee: The Regents of the University of California, Oakland, CA (US)

(*) Notice: Subject to any disclaimer, the term of this patent is extended or adjusted under 35 U.S.C. 154(b) by 302 days.

(21) Appl. No.: 15/467,099

(22) Filed: Mar. 23, 2017

(65) Prior Publication Data
US 2017/0279122 A1    Sep. 28, 2017

Related U.S. Application Data

(60) Provisional application No. 62/312,369, filed on Mar. 23, 2016.

(51) Int. Cl.
*H01M 4/60* (2006.01)
*C08G 73/14* (2006.01)
(Continued)

(52) U.S. Cl.
CPC ............... *C08L 79/08* (2013.01); *C08K 3/04* (2013.01); *C08K 3/06* (2013.01); *C08K 9/04* (2013.01);
(Continued)

(58) Field of Classification Search
CPC ....... H01M 4/622; H01M 4/136; C08L 79/08; C08L 2203/20; C08K 9/04; C08K 2201/001; C07D 471/06
See application file for complete search history.

(56) References Cited

U.S. PATENT DOCUMENTS

| 2011/0268647 A1 | 11/2011 | Ivanovici et al. |
| 2012/0088154 A1 | 4/2012 | Liu et al. |
(Continued)

FOREIGN PATENT DOCUMENTS

| WO | 2011159922 A2 | 12/2011 |
| WO | 2013023216 A1 | 2/2013 |
(Continued)

OTHER PUBLICATIONS

Kozhemyakina et al., "Non-Covalent Chemistry of Graphene: Electronic COmmunication with Dendronized Perylene Bisimides," 2010, Adv. Mater., 22, 5483-5487. (Year: 2010).*
(Continued)

*Primary Examiner* — Ula C Ruddock
*Assistant Examiner* — Matthew W Van Oudenaren
(74) *Attorney, Agent, or Firm* — Robin C. Chiang; Stuart B. Chinn; Lawrence Berkeley National Laboratory

(57) ABSTRACT

To address the need for multi-functional binders specifically tailored for sulfur cathodes π-stacked perylene bisimide (PBI) molecules are repurposed as redox-active supramolecular binders in sulfur cathodes for Li—S cells. In operando lithiation of PBI binders permanently reduces Li—S cell impedance enabling high-rate cycling, a critical step toward unlocking the full potential of Li—S batteries.

28 Claims, 12 Drawing Sheets

(51) Int. Cl.

| | |
|---|---|
| *C08K 3/04* | (2006.01) |
| *C08K 3/06* | (2006.01) |
| *C08K 9/04* | (2006.01) |
| *C08L 27/16* | (2006.01) |
| *C08L 79/08* | (2006.01) |
| *H01M 10/052* | (2010.01) |
| *H01M 10/0567* | (2010.01) |
| *H01M 10/0568* | (2010.01) |
| *H01M 10/0569* | (2010.01) |
| *H01M 4/36* | (2006.01) |
| *H01M 4/62* | (2006.01) |
| *H01M 4/66* | (2006.01) |
| *H01M 4/02* | (2006.01) |
| *H01M 4/38* | (2006.01) |
| *H01M 4/136* | (2010.01) |
| *C07D 471/06* | (2006.01) |

(52) U.S. Cl.
CPC ............ *H01M 4/364* (2013.01); *H01M 4/38* (2013.01); *H01M 4/623* (2013.01); *H01M 4/625* (2013.01); *H01M 4/661* (2013.01); *H01M 10/052* (2013.01); *H01M 10/0567* (2013.01); *H01M 10/0568* (2013.01); *H01M 10/0569* (2013.01); *C07D 471/06* (2013.01); *C08K 2201/001* (2013.01); *C08L 2203/20* (2013.01); *H01M 4/136* (2013.01); *H01M 4/622* (2013.01)

(56) References Cited

U.S. PATENT DOCUMENTS

| | | | | |
|---|---|---|---|---|
| 2013/0065128 | A1* | 3/2013 | Li | H01M 10/0525 429/218.1 |
| 2014/0234702 | A1* | 8/2014 | Zhang | H01M 4/583 429/199 |
| 2016/0141620 | A1* | 5/2016 | Cairns | H01M 4/133 429/200 |

FOREIGN PATENT DOCUMENTS

| | | | |
|---|---|---|---|
| WO | 2013049663 A1 | | 4/2013 |
| WO | 2015065539 A2 | | 5/2015 |
| WO | WO2015065539 | * | 5/2015 |

OTHER PUBLICATIONS

Rao et al., Porous carbon-sulfur composite cathode for lithium/sulfur cells, Electrochemistry Communications, Apr. 2012, 13, 1-5 (Year: 2012).

International Search Report and Written Opinion dated Jun. 25, 2015, for PCT/US2014/043503, 8 pages.

* cited by examiner

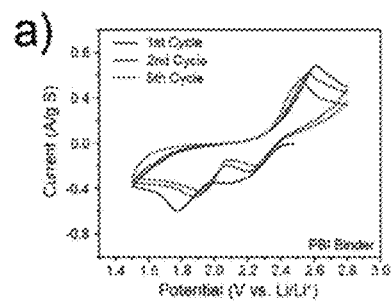
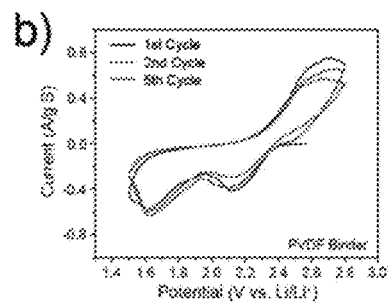
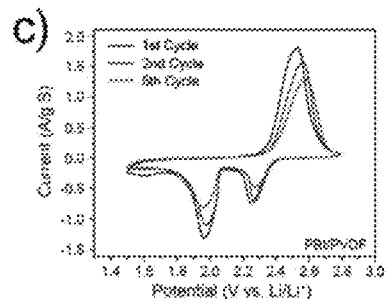
Fig. 2A  Fig. 2B  Fig. 2C
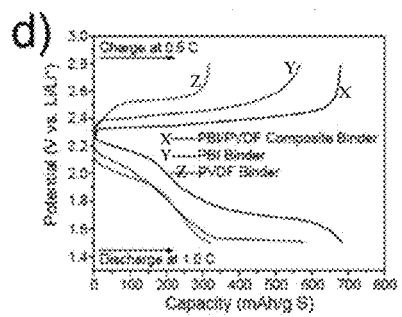
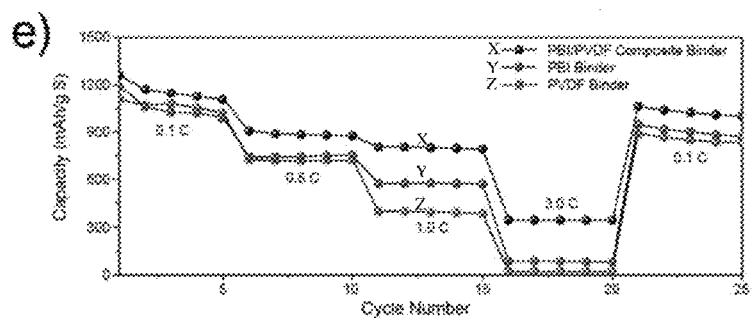
Fig. 2D  Fig. 2E
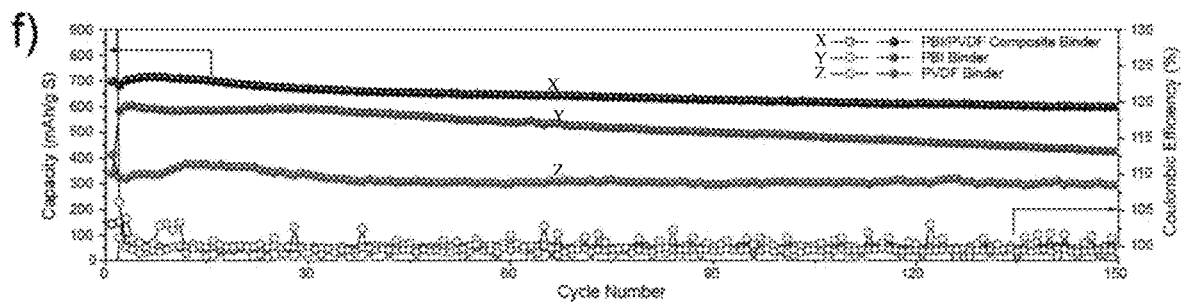
Fig. 2F

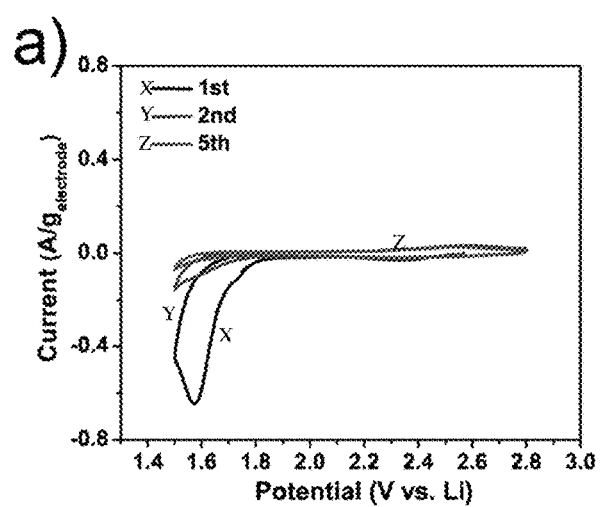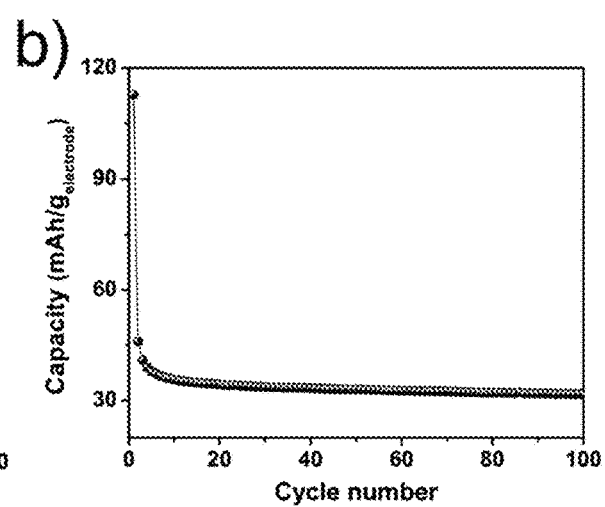
Fig. 12A
Fig. 12B

REDOX-ACTIVE SUPRAMOLECULAR POLYMER BINDERS DERIVED FROM PERYLENE BISIMIDE NANOWIRES ENABLE HIGH-RATE LITHIUM-SULFUR BATTERIES

CROSS REFERENCE TO RELATED APPLICATIONS

This application claims priority to U.S. Provisional Application Ser. No. 62/312,369 filed Mar. 23, 2016, which application is incorporated herein by reference as if fully set forth in their entirety. This application is related to co-pending U.S. application Ser. No. 14/899,997.

STATEMENT OF GOVERNMENTAL SUPPORT

The invention described and claimed herein was made in part utilizing funds supplied by the U.S. Department of Energy under Contract No. DE-AC02-05CH11231 between the U.S. Department of Energy and the Regents of the University of California for the management and operation of the Lawrence Berkeley National Laboratory. The government has certain rights in this invention.

BACKGROUND OF THE INVENTION

Field of the Invention

The present invention relates to the field of Lithium-Sulfur Batteries.

Related Art

Breakthroughs in electrochemical energy storage that enable energy-dense, high-power, and low-cost storage are necessary to catalyze a societal shift from fossil fuels to a carbon-neutral future powered by renewable energy. Of the forward-looking battery chemistries, lithium-sulfur (Li—S) cells are well poised to usurp the dominance of Li-ion owing to the high theoretical specific capacity of the sulfur cathode (1675 mAh $g^{-1}$ vs. 272 mAh $g^{-1}$ for a $LiCoO_2$ cathode), the low cost of sulfur (<$200 $ton^{-1}$), the low environmental impact of sulfur, and the improved safety of the cell. Nevertheless, persistent challenges associated with the sulfur cathode must be overcome for Li—S cells to become practical. Namely, while sulfur cathodes have been engineered extensively for high energy density and durability, design rules are still lacking for high power while also attaining high specific energy.

BRIEF DESCRIPTION OF THE DRAWINGS

The foregoing aspects and others will be readily appreciated by the skilled artisan from the following description of illustrative embodiments when read in conjunction with the accompanying drawings.

FIGS. 2A-2C illustrate cyclic voltammograms and electrochemical performances of the PBI, PVDF and PBI/PVDF composite binder cathodes. Cyclic voltammograms of the PBI, PVDF and PBI/PVDF composite binder cathodes at a scan rate of 0.1 mV $s^{-1}$. FIG. 2D illustrates voltage profiles of the PBI, PVDF, and PBI/PVDF composite binder cathodes at the second cycle. FIG. 2E illustrates rate capability of the PBI, PVDF and PBI/PVDF, composite binder cathodes. The charge C-rate was fixed at 0.1 C. FIG. 2F illustrates cycling performances and coulombic efficiency of the PBI, PVDF, and PBI/PVDF composite binder cathodes at 1.0 C discharge.

FIG. 12A illustrates a cyclic voltammogram and FIG. 12B illustrates cycling performance of the PBI cathode without S-GO nanocomposite. CV was conducted at 0.1 mV $s^{-1}$ and the cathode was galvanostatically discharged at 1.0 A per $g_{electrode}$.

DETAILED DESCRIPTION

In the discussions that follow, various process steps may or may not be described using certain types of manufacturing equipment, along with certain process parameters. It is to be appreciated that other types of equipment can be used, with different process parameters employed, and that some of the steps may be performed in other manufacturing equipment without departing from the scope of this invention. Furthermore, different process parameters or manufacturing equipment could be substituted for those described herein without departing from the scope of the invention.

These and other details and advantages of the present invention will become more fully apparent from the following description taken in conjunction with the accompanying drawings.

Various embodiments of the invention show that transport bottlenecks for ions and electrons in composite sulfur cathodes, presently limiting high-power applications, can be relieved when the conventional polymer binder is supplanted with a custom-purposed supramolecular polymer binder that is also a redox-mediator for the sulfur battery chemistry.

Figure 1A:
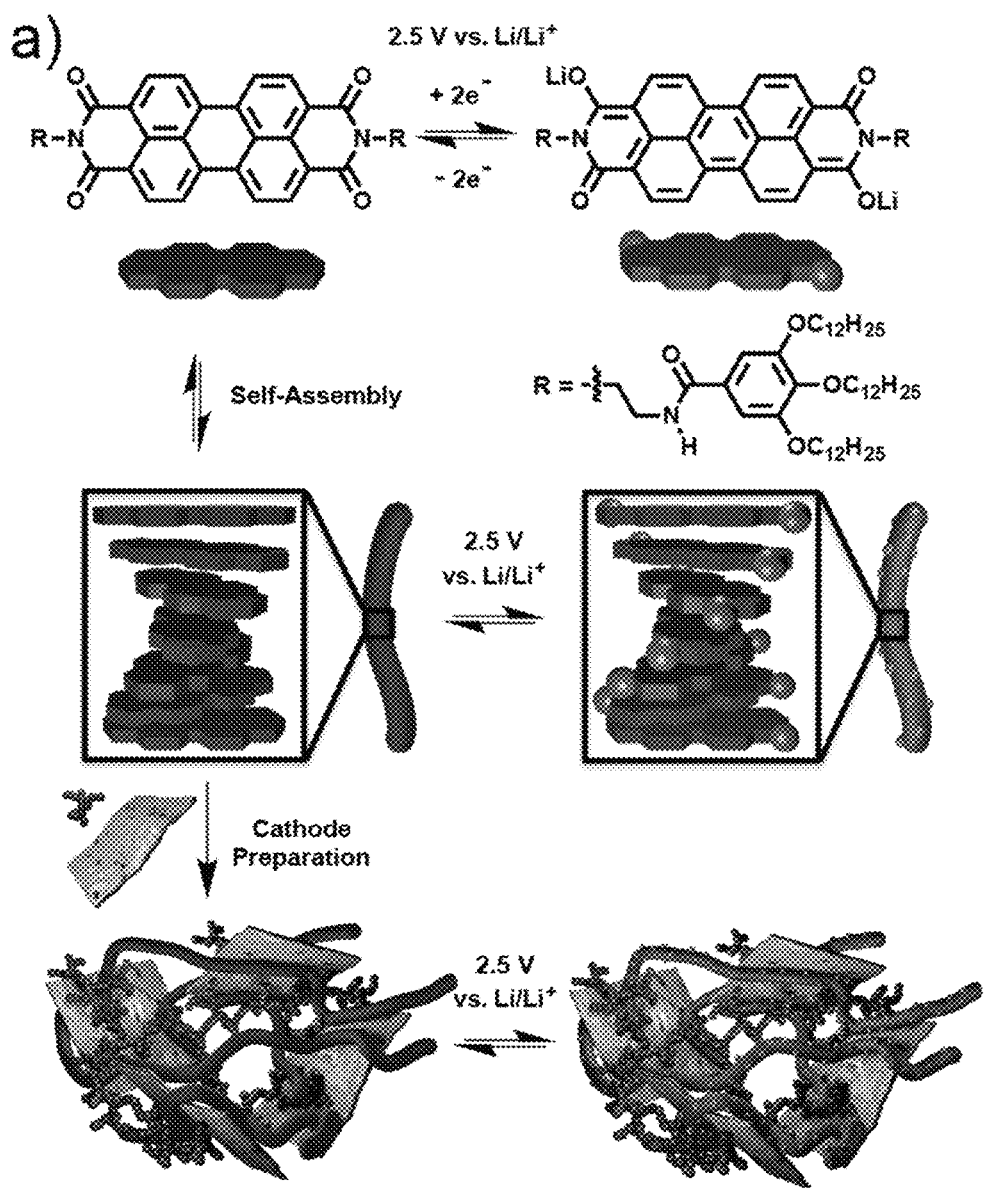
FIG. 1A illustrates an overview of perylene bisimide (PBI) redox chemistry, self-assembly of PBI into supramolecular polymers through π-stacking, cathode preparation with Ketjenblack (KB) and sulfur on graphene oxide (S-GO), and in operando redox activation of the PBI binder in a functioning cathode. The neutral PBI binder is activated to a dianionic state ($Li_2$-PBI) upon reduction at 2.5 V vs. $Li/Li^+$.
Figures 1B, 1C, 1D:
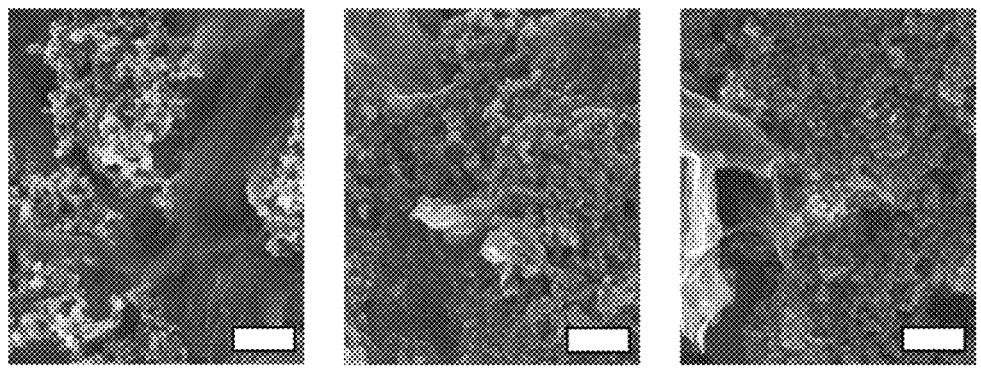
FIG. 1B illustrates a SEM image of a PBI cathode showing bundles of supramolecular polymer wires dispersed with KB and S-GO.
FIG. 1C illustrates a SEM image of a PVDF cathode with KB and S-GO.
FIG. 1D illustrates a SEM image of a the PBI/PVDF cathode with KB and S-GO. Scale bars represent 400 nm.

FIG. 1A illustrates an overview of perylene bisimide (PBI) redox chemistry, self-assembly of PBI into supramolecular polymers through π-stacking, cathode preparation with Ketjenblack (KB) and sulfur on graphene oxide (S-GO), and in operando redox activation of the PBI binder in a functioning cathode. The neutral PBI binder is activated to a dianionic state ($Li_2$-PBI) upon reduction at 2.5 V vs. Li/Li$^+$. FIG. 1B illustrates a SEM image of a PBI cathode showing bundles of supramolecular polymer wires dispersed with KB and S-GO; FIG. 1C illustrates a SEM image of a PVDF cathode with KB and S-GO; FIG. 1D illustrates a SEM image of a the PBI/PVDF cathode with KB and S-GO. Scale bars represent 400 nm.

These supramolecular redox mediators consist of n-stacked perylene bisimide (PBI) molecules, which are reduced electrochemically in operando during the first discharge at potentials below 2.5 V vs. Li/Li$^+$. We show that upon activation, the cell impedance is dramatically reduced and commensurate with stable cycling at both moderate and high rates. We also note unexpected synergies between these redox-mediating supramolecular binders and conventional polymer binders when both are present in the sulfur cathode. These synergies manifest as a powerful new means to direct the evolution of cell impedance to a state that is lower than cells assembled with either of the binders on their own; furthermore, we show that this state of the battery is sustainable indefinitely throughout high-rate cycling. Our work highlights the multi-faceted role played by these underappreciated components in the sulfur cathode, and where new concepts in adaptive materials can be applied to solve challenges in charge transport.

Binders for composite sulfur cathodes should aid in film processing and drying onto aluminum current collectors, electrolyte wetting during cell assembly, ion transport, and mechanical integrity upon cycling to accommodate the volume changes associated with $S_8$—$Li_2S$ interconversion. Polyvinylidene difluoride (PVDF) is the most prevalent binder used today, although recent reports have suggested that PVDF can block the pores of mesostructured conductive carbons, which negatively impacts the available surface area for $Li_2S$ electrodeposition. Alternative binders—including gelatin, polyvinylpyrrolidone (PVP), PVP blends with Nafion, PAMAM dendrimers, polycationic β-cyclodextrins, polyacrylic acid, polyethylene oxide, and carboxymethylcellulose:styrenebutadiene-rubber (CMC:SBR) have therefore focused on addressing one or more of these binder attributes as a means to improve cathode performance.

Some of the most successful binders have been shown to mitigate the migration of soluble polysulfides from the cathode into the electrolyte, which otherwise would lead to stranded sulfur in the cell or instabilities in the lithium anode. None have been reported that directly participate in the redox chemistry of sulfur or otherwise serve to enhance ion transport as needed for high-rate applications.

Nonetheless, we hypothesize that these attributes are critical to the further advancement of the sulfur cathode. Our perspective is that these functions can now be conferred to new binder materials based on supramolecular redox mediators. Supramolecular redox mediators offer both self-healing properties needed to accommodate the volume changes in the sulfur cathode on cycling and adaptive charge transport upon activation. Their role as such remains distinctive from electronically conductive polymers used to confine sulfur.

Figure 5:
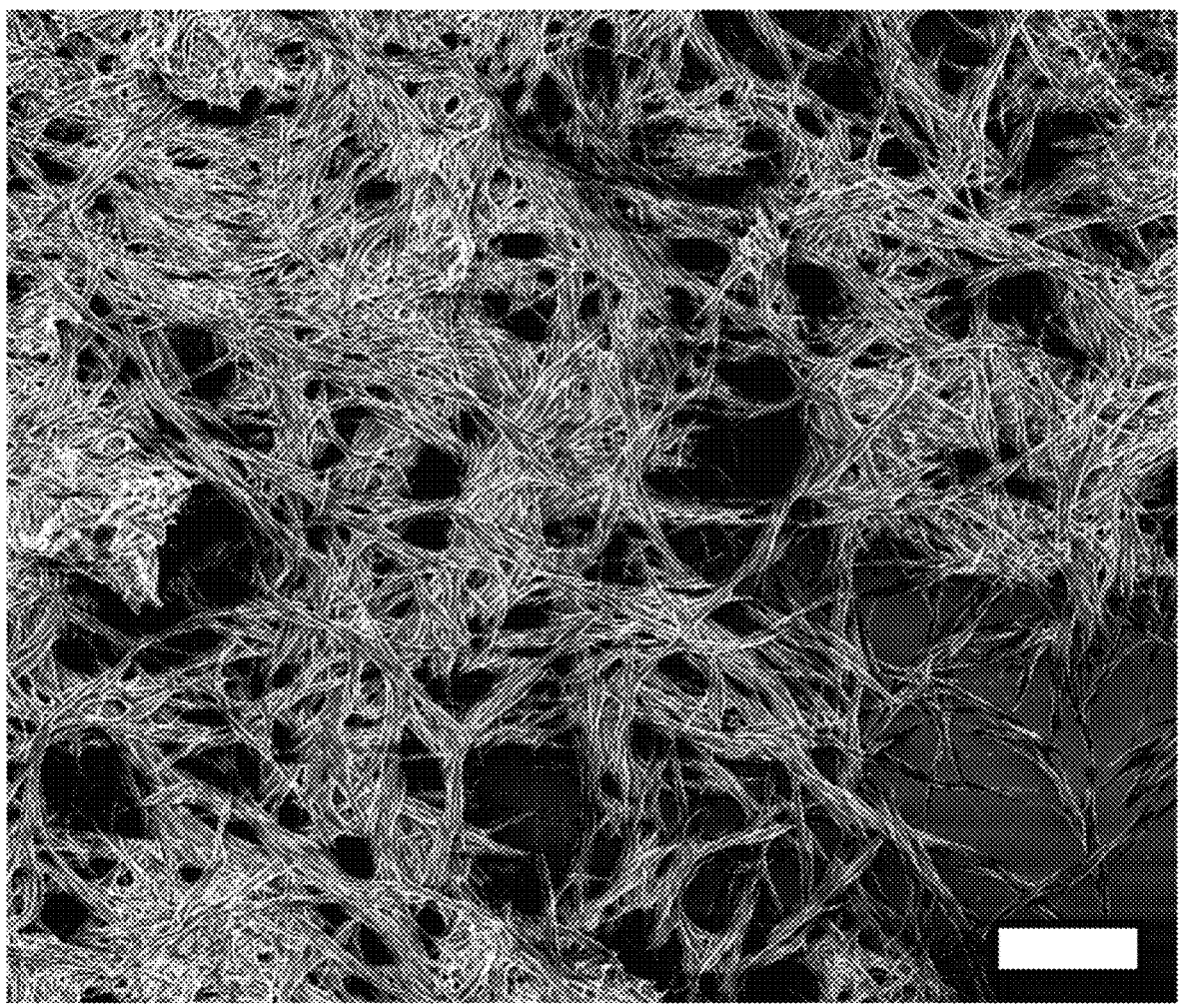
FIG. 5 illustrates a SEM of a PBI suspension dropcast from 1,3-dioxolane onto a silicon wafer. The scale bar is 10 μm.
Figure 8:
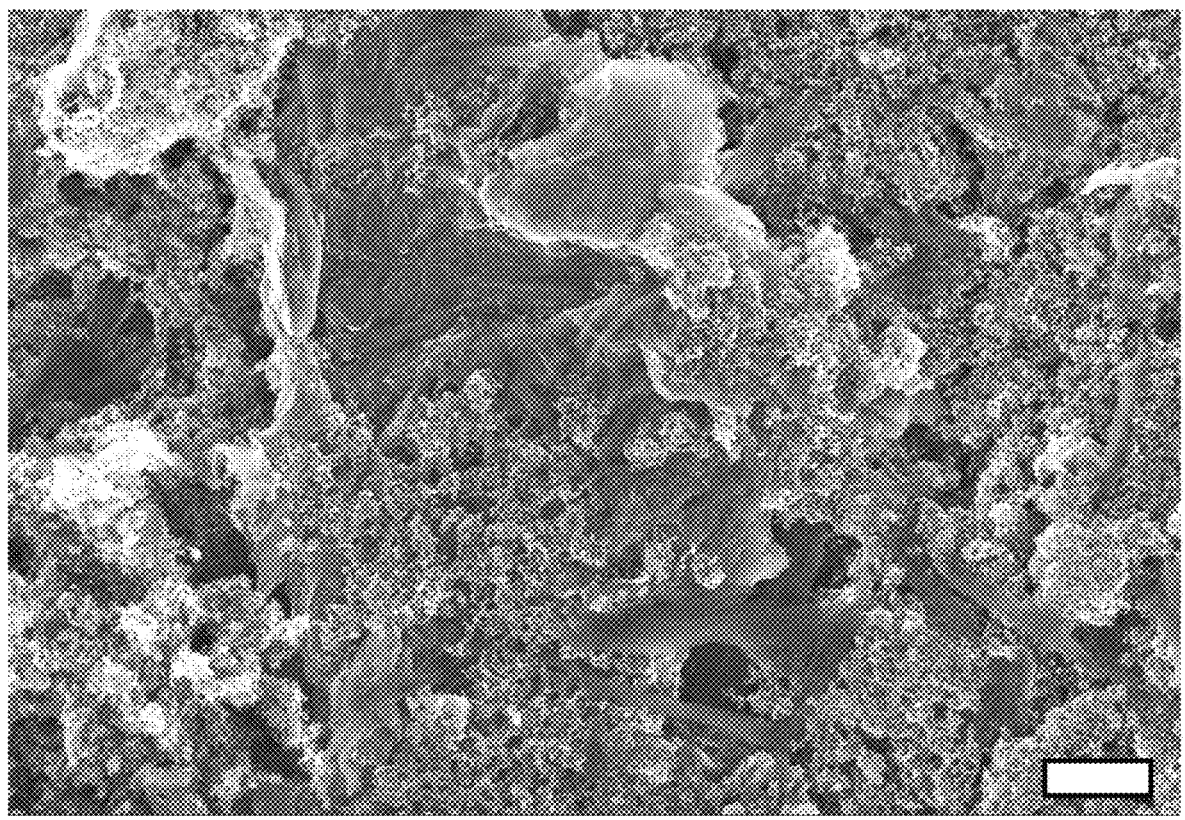
FIG. 8 illustrates SEM of the PBI cathode. Fibrous supramolecular bundles of π-stacked PBI are visible. The scale bar is 2 μm.
Figure 9:
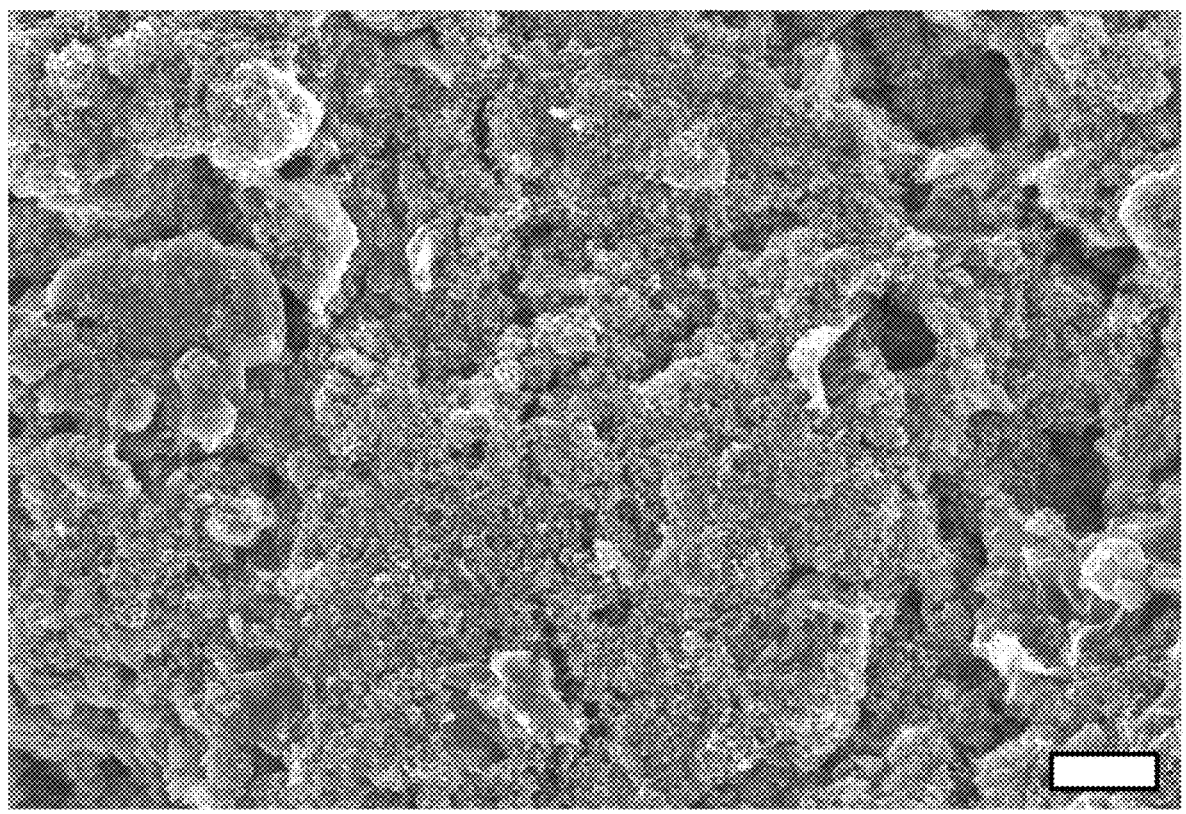
FIG. 9 illustrates a SEM of the PVDF cathode. The scale bar is 2 μm.
Figure 10:
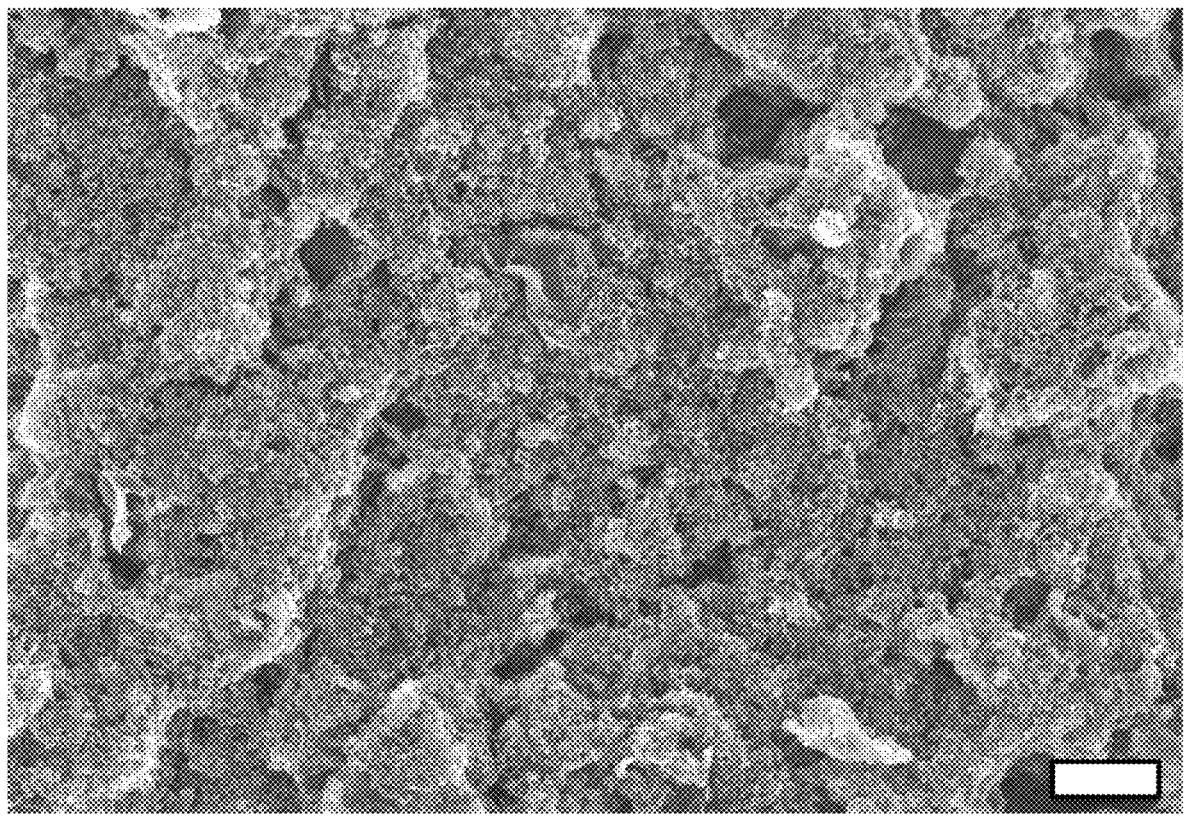
FIG. 10 illustrates a SEM of the PBI/PVDF composite cathode. The scale bar is 2 μm.

Redox mediators for sulfur cathode reactions, which nominally occur at 2.5 V and 2.1 V vs. Li/Li$^+$, have only been recently reported. Those consisting of polycyclic aromatic hydrocarbons, and in particular perylene bisimide (PBI) and benzo[ghi]perylene imide (BPI), are amenable to supramolecular polymerization via π-stacking. Whereas previous accounts focused on the action of soluble redox mediators in Li—S cells, our focus here is instead on their action in the solid state as a binder. We were ultimately successful in sequestering PBI-based redox-mediators as self-assembled networks of nanowires, tens of microns in length, in a composite sulfur cathode by careful selection of the imide substituents inspired by Würthner and co-workers. The networked PBI binder architecture—readily apparent in the solid state (see FIG. 5) as well as in the cathode composite (see FIG. 1C and FIG. 8)—remained intact upon electrolyte infiltration.

The redox-active PBI core of our supramolecular binder exhibits a fully reversible two-electron reduction around 2.5 V vs. Li/Li$^+$ (see FIG. 1A), which aids in charge transfer to and from polysulfides in Li—S cells. Additionally, their manifestation as a percolated network suggests highly structured regions within the cathode that are both lithiated and solvated. We anticipate that this architecture helps localize Li$^+$ ions near active material as needed for high interfacial ion flux. We were also interested in mixed-binder approaches consisting of PBI/PVDF blends in that each component features complementary coordination for Li$^+$ (which is oxo-phillic, favoring PBI) and TFSI$^-$ (which is fluorophillic, favoring PVDF), respectively; this unusual complementarity could enable higher mobility for ionic charge carriers in the composite sulfur cathode.

Figure 6:
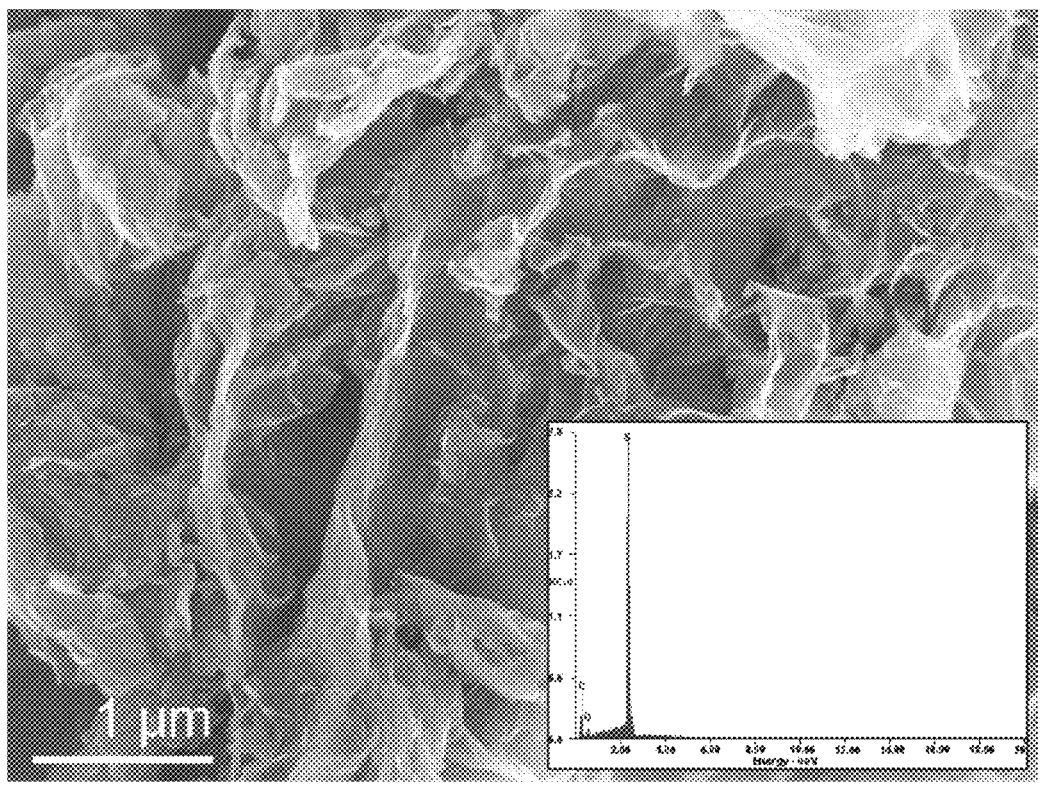
FIG. 6 illustrates a SEM image of an S-GO nanocomposite with the EDS spectrum.
Figure 7:
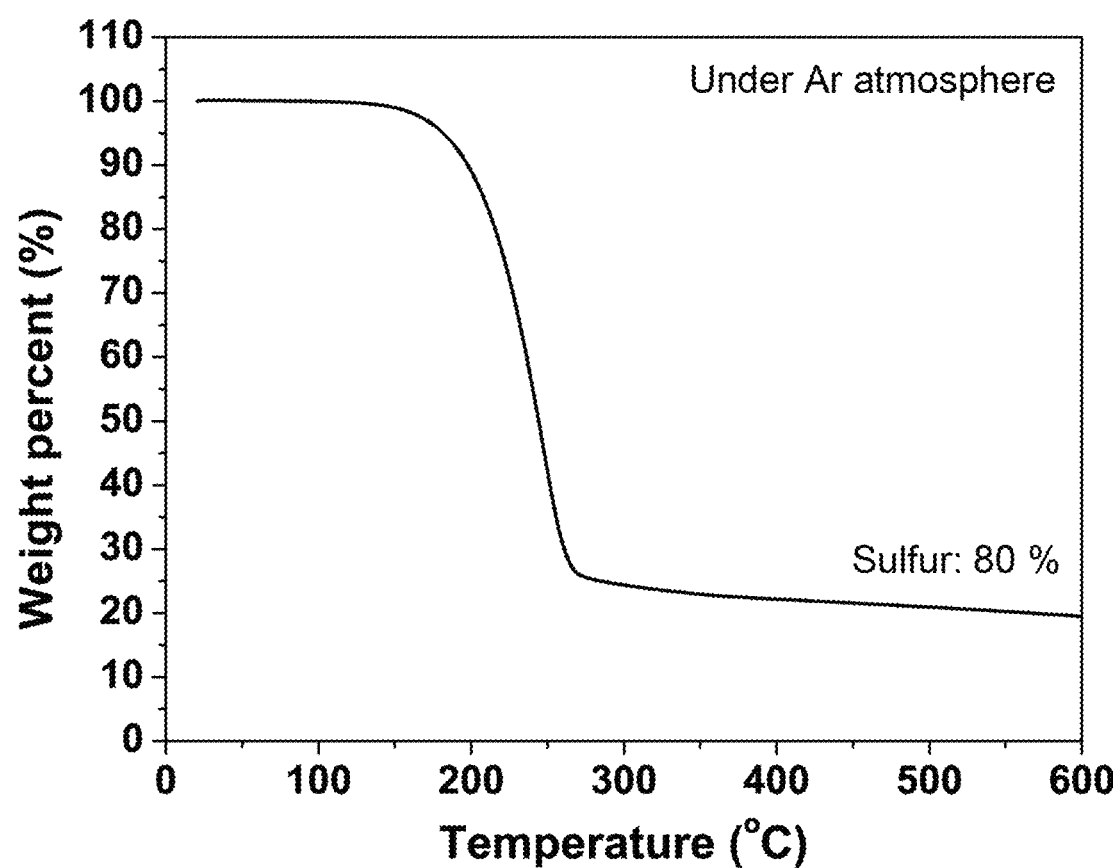
FIG. 7 illustrates TGA result of the S-GO nano-composite under Ar atmosphere with a temperature ramping rate of 5° C. $min^{-1}$.

To demonstrate the performance-enhancing features of PBI supramolecular polymers in Li—S cells, we interfaced them with a cetyltrimethyl ammonium bromide (CTAB)-modified sulfur-graphene oxide (S-GO) nanocomposite (80% S w/w, see FIGS. 6-7) as the active material in the cathode.

Three distinctive cathodes were prepared using CTAB modified S-GO, Ketjenblack (KB) as conductive carbon additive, and various binders in a 8:1:1 weight ratio; binders included pure PBI nanowire networks, pure PVDF, and a 1:1 blend of PBI and PVDF (PBI/PVDF). Slurries of these components in N-methyl-2-pyrrolidinone (NMP) were coated onto aluminum current collectors by doctor-blade coating and yielded cathodes with a sulfur content of 64% (w/w) after drying.

Scanning electron micrographs of each composite sulfur cathode indicated macroscopic film homogeneity, however, differences in the PBI network architecture were observed for cathodes prepared using PBI when compared to those prepared using PBI/PVDF blends (see FIGS. 1B-1D and FIGS. 8-10). More specifically, the introduction of PVDF to the PBI cathode appears to disrupt the bundling of PBI nanowires in the solid state, indicative of high interfacial area between the two materials as well as higher interfacial area with S-GO and KB. Reduced bundling of PBI nanowires in the PBI/PVDF cathode also improved the bulk electrolyte wettability relative to the PBI cathode (see FIG. 11).

FIGS. 2A-2C illustrate cyclic voltammograms and electrochemical performances of the PBI, PVDF and PBI/PVDF composite binder cathodes. Cyclic voltammograms of the PBI, PVDF and PBI/PVDF composite binder cathodes at a scan rate of 0.1 mV s$^{-1}$. FIG. 2D illustrates voltage profiles of the PBI, PVDF, and PBI/PVDF composite binder cathodes at the second cycle. FIG. 2E illustrates rate capability of the PBI, PVDF and PBI/PVDF, composite binder cathodes. The charge C-rate was fixed at 0.1 C. FIG. 2F illustrates cycling performances and coulombic efficiency of the PBI, PVDF, and PBI/PVDF composite binder cathodes at 1.0 C discharge.

The electrochemical behavior of sulfur cathodes prepared with PBI, PVDF, or PBI/PVDF binders was investigated using cyclic voltammetry (CV) over the potential range 1.5-2.8 V vs. Li/Li$^+$ and at a scan rate of 0.1 mV s$^{-1}$ (see FIGS. 2A-2C). All three cathodes showed two reduction peaks and one oxidation peak during the discharge and charge processes, respectively.

However, the CV peak characteristics of the three cathodes were significantly different. After the first cycle, two reduction peaks and an anodic peak of the PBI cathode were located at 2.3, 1.9 V and 2.6 V, respectively (see FIG. 2A), whereas those of the PVDF cathode were located at 2.1, 1.6 V and 2.7 V (see FIG. 2B), indicating that larger peak shifts occurred in the CV of the PVDF cathode than that of the PBI cathode due to the larger overpotential of the PVDF cathode.

Moreover, the redox peaks in the CV for the PVDF cathode were broader and less distinguishable than those of the PBI cathode. The incomplete anodic peak of the PVDF cathode is especially noteworthy and reflects the slow reaction kinetics of the PVDF cathode. In contrast, the PBI/PVDF composite binder cathode exhibited the lowest overpotential with sharp peaks located at 2.3 V and 2.0 V for the cathodic peaks and at 2.55 V for the anodic peak, indicating that the highest reaction rate for the sulfur cathode is facilitated by the PBI/PVDF binder blend.

To evaluate the impact of these distinctive electrochemical behaviors on cell performance, PBI, PVDF, and PBI/PVDF composite binder cathodes were galvanostatically cycled at 1.0 and 0.5 C (1.0 C=1672 mA g$^{-1}$ S) for the discharge and charge processes, respectively (see FIG. 2D). During the discharge process at 1.0 C, the PBI cathode showed two major discharge plateaus with a capacity of 582 mAh g$^{-1}$ S, whereas the PVDF cathode showed no obvious second plateau associated with the formation of Li$_2$S, which caused a low sulfur utilization of only 323 mAh g$^{-1}$ S. On the other hand, the PBI/PVDF composite cathode delivered the highest discharge specific capacity of 700 mAh g$^{-1}$ S with the lowest discharge and charge overpotentials during the cycle.

The rate capabilities of PBI, PVDF, and PBI/PVDF composite binder cathodes were also evaluated at various discharge C rates from 0.1 C to 3.0 C and then back to 0.1 C. At 0.1 C, both the PBI and PVDF cathodes showed similar specific discharge capacities of about 1050 mAh g$^{-1}$ S, however, the specific discharge capacity of the PVDF cathode decreased dramatically as the test C-rate increased, and finally, a specific discharge capacity of only about 320 mAh g$^{-1}$ S was obtained at 1.0 C discharge.

In contrast, the PBI cathode retained a specific discharge capacity of about 600 mAh g$^{-1}$ S at 1.0 C discharge, indicating that the PBI cathode could provide an electrode structure more suitable for high C-rates than the PVDF cathode. Furthermore, the PBI/PVDF composite binder cathode exhibited the best rate capability with a highly reversible discharge capacity of about 800 and 350 mAh g$^{-1}$ S at C-rates of 1.0 and 3.0 C, respectively, and the specific discharge capacity recovered quickly to 1066 mAh g$^{-1}$ S, when the C-rate was decreased back to 0.1 C.

To understand the longevity of Li—S cells configured with the different binders, cycling performance at 1.0 C over 150 cycles was evaluated for PBI, PVDF, and PBI/PVDF derived cathodes (see FIG. 2F). Compared to the PVDF cathode, the PBI cathode exhibited a reversible discharge capacity approximately 1.5-2 times higher after 150 cycles with a Coulombic efficiency above 99.4%. The Coulombic efficiency of the PVDF cathode was unstable, possibly due to incomplete Li$_2$S formation, accounting for the lack of a second discharge plateau shown in FIG. 2D.

On the other hand, the PBI/PVDF composite binder cathode exhibited excellent cycling performance at 1.0 C discharge with an initial discharge capacity around 700 mAh g$^{-1}$ S. A specific discharge capacity of 600 mAh g$^{-1}$ S was obtained after 150 cycles, which corresponds to a capacity retention of 86%. During 150 cycles, the Coulombic efficiency of the PBI/PVDF composite binder cathode was above 99.8%, reflecting the superior reversibility of the electrochemical reaction between sulfur and lithium during cycling with this binder blend.

Collectively, these initial experiments point to impressive gains in high-rate performance when PBI is used as a binder in place of PVDF, and even greater gains when the PBI/PVDF blend is used. While there is a myriad of microscopic processes that dictate Li—S cell characteristics, the presence of these new PBI binders with turn-on activation for charge transfer and charge transport only amplifies that complexity as does the role played by PBI/PVDF interfaces. Thus, we were interested in applying additional electroanalytical techniques to our cathodes that might more directly relate the specific influence of the adaptive charge-transporting PBI networks on the observed cell performance.

Figure 3A:
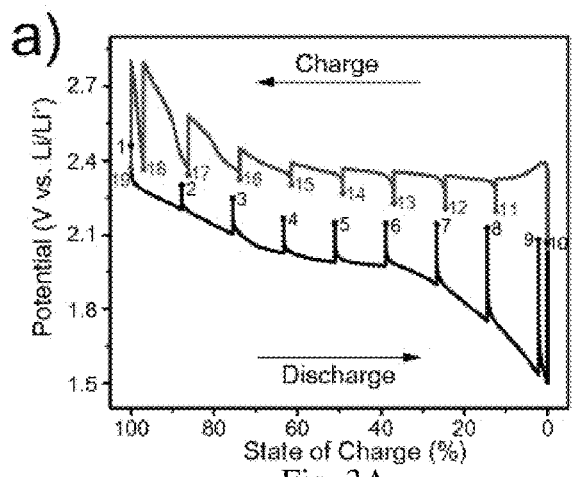
FIGS. 3A-3C illustrate voltage profiles of PBI, PVDF and PBI/PVDF composite binder cathodes at 0.1 C. Cathodes were discharged or charged in stages for 45 min, followed by 1 h of equilibration time. (0% SOC is relative to the specific discharge capacity of the cathode at the end of discharge). Points are numbered in conjunction with data discussed in FIGS. 4A-4F.
Figure 3B:
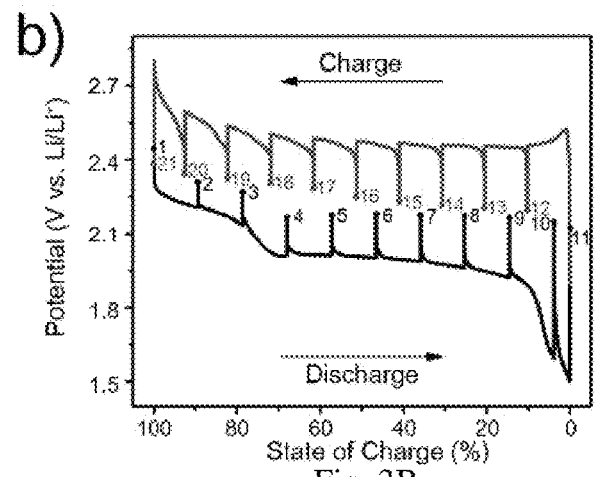
Figure 3C:
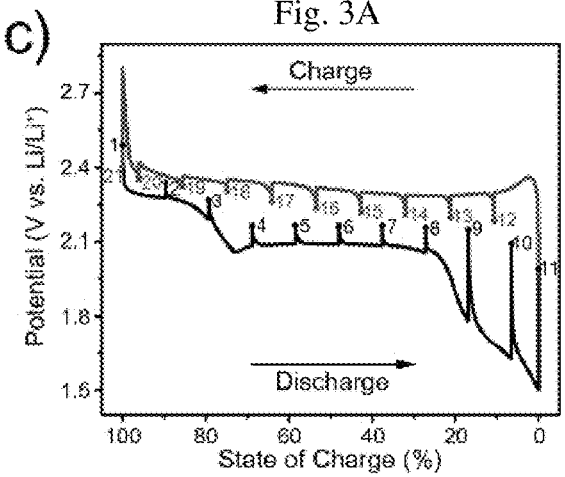
Figure 3D:
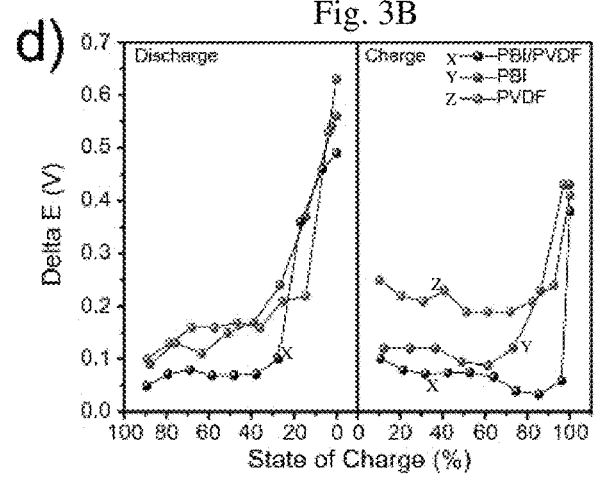
FIG. 3D illustrates a plot of polarization overpotential measured between the end of the current step and the end of the relaxations step.

FIGS. 3A-3C illustrate voltage profiles of PBI, PVDF and PBI/PVDF composite binder cathodes at 0.1 C. Cathodes were discharged or charged in stages for 45 min, followed by 1 h of equilibration time. (0% SOC is relative to the specific discharge capacity of the cathode at the end of discharge). Points are numbered in conjunction with data discussed in FIGS. 4A-4F. FIG. 3D illustrates a plot of polarization overpotential measured between the end of the current step and the end of the relaxations step.

To that end, we applied a galvanostatic intermittent titration technique (GITT) to study the evolution of ion-transport behaviors within the cathodes upon cycling. PBI, PVDF, and PBI/PVDF composite binder cathodes were cycled at 0.1 C with 45-min-long galvanostatic pulses, interrupted by 1 h of equilibration time between pulses (see FIGS. 3A-3C). Overpotentials at each point, determined by the potential difference between the end of the current step and the end of the equilibration step, are plotted as ΔE vs. state of charge (SOC) (see FIG. 3D). From these data, it was readily apparent that the open circuit potentials measured after the equilibration times were equivalent for all three cathodes; however, the hysteresis of the cathodes were significantly different. In principle, the sudden potential change at short times is mainly due to an iR drop generated by the ohmic resistance of the cell, and the PVDF cathode showed the highest overpotential at nearly all states of charge compared to the other two cathodes containing supramolecular PBI binder (see FIG. 3D).

Notably, the PBI/PVDF blended binder cathode showed the lowest overpotential among all cathodes. At SOCs between 20-0% and 80-100% during discharge and charge processes, respectively, all three cathodes showed dramatic increases in the overpotential. In those regions, dissolved lithium polysulfides are re-deposited onto the embedded current collector surface, essentially forming insoluble $Li_2S$ or sulfur films during discharge or charge, respectively. This deposition increases the internal resistance of the cell by impeding both electron and lithium ion conduction due to their insulating nature. Although PBI and PVDF cathodes each show similar overpotentials during the initial discharge, there is a pronounced drop in charging overpotentials for the PBI cathode once it has been electrochemically activated, indicating a redox-mediating effect or, alternatively, a change in the local solvation of the PBI network upon reduction and lithiation.

FIGS. 4A-4F illustrate nyquist plots of the PVDF cathode during discharge (FIG. 4A) and charge (FIG. 4B), PBI cathode during discharge (FIG. 4C) and charge (FIG. 4D), and PBI/PVDF composite binder cathode during discharge (FIG. 4E) and charge (FIG. 4F) in the frequency range of 10 mHz to 1 MHz. Numbered spectra correspond to the points labeled in FIGS. 3A-3C.

Further insight into the emergent in operando behavior unique to cathodes prepared with PBI binders was gleaned from EIS measured at the end of every equilibration step throughout the GITT analysis (see FIGS. 4A-4F). Nyquist plots of the PVDF cathode showed relatively large, depressed semicircles that increased in diameter as the SOC approached 0% and returned to near the original diameter upon charging to 100% SOC (see FIGS. 4A-4B), likely due to deposition and then dissolution of insulating $Li_2S$.

Figure 4A:
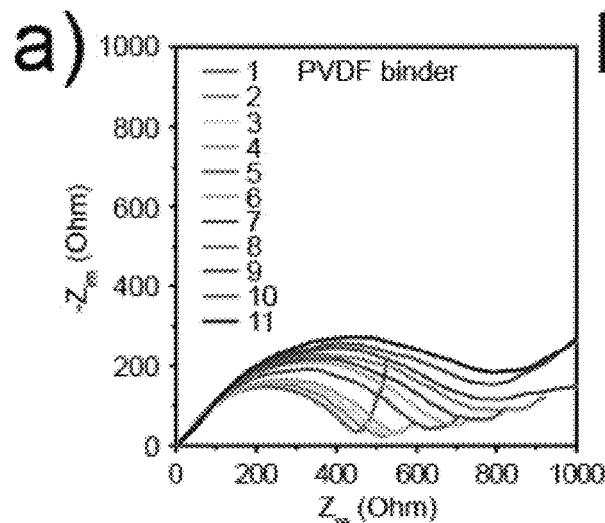
FIGS. 4A-4F illustrate nyquist plots of the PVDF cathode during discharge (FIG. 4A) and charge (FIG. 4B), PBI cathode during discharge (FIG. 4C) and charge (FIG. 4D), and PBI/PVDF composite binder cathode during discharge (FIG. 4E) and charge (FIG. 4F) in the frequency range of 10 mHz to 1 MHz. Numbered spectra correspond to the points labeled in FIGS. 3A-3C.
Figure 4B:
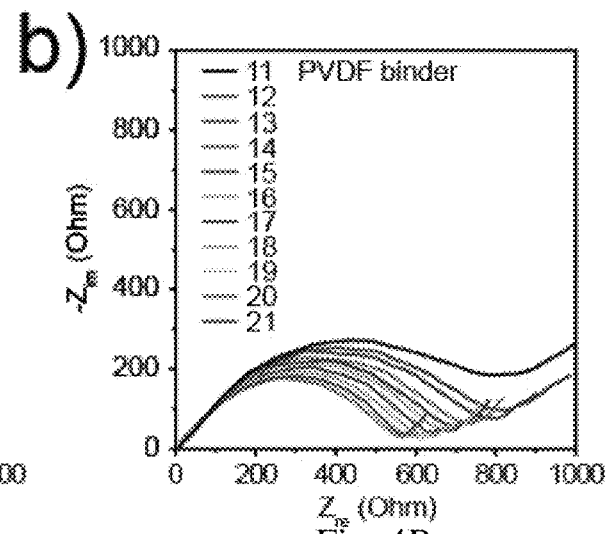
Figure 4C:
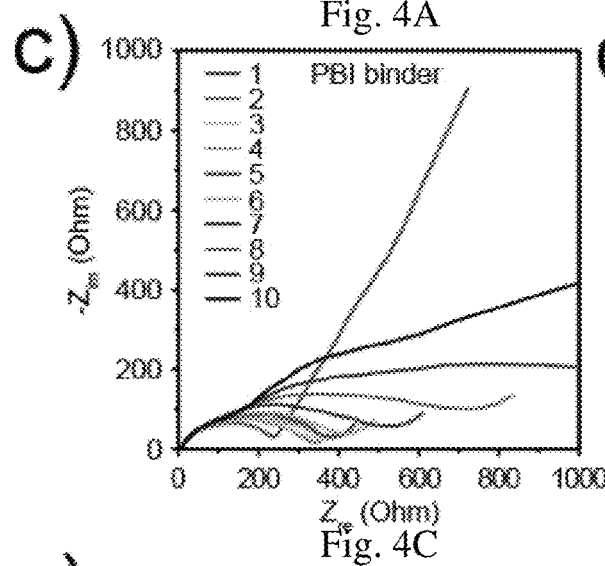
Figure 4D:
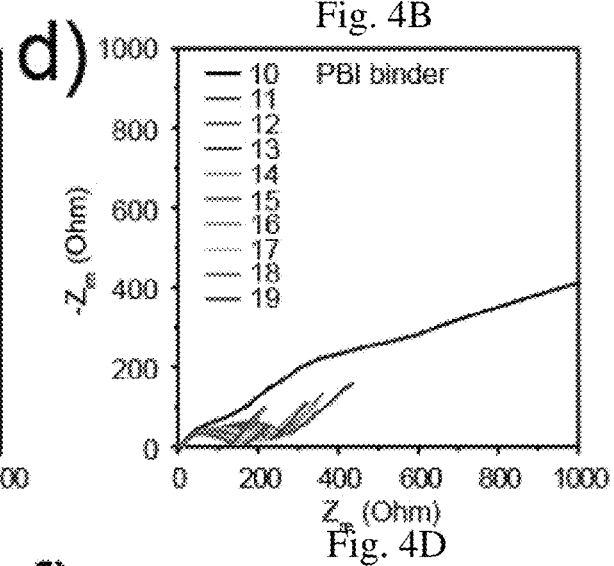
Figure 4E:
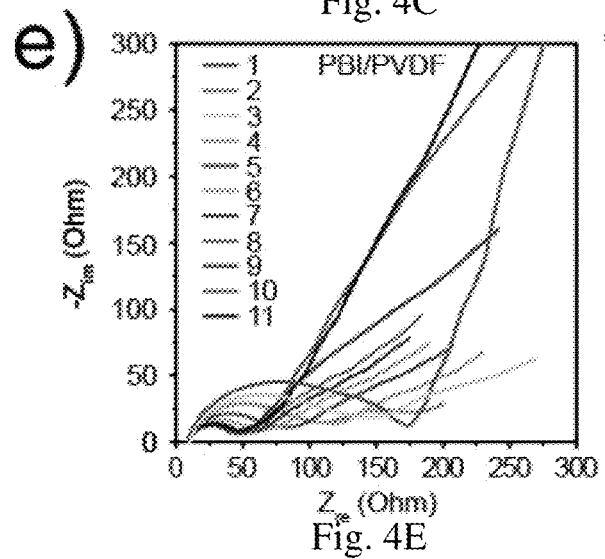
Figure 4F:
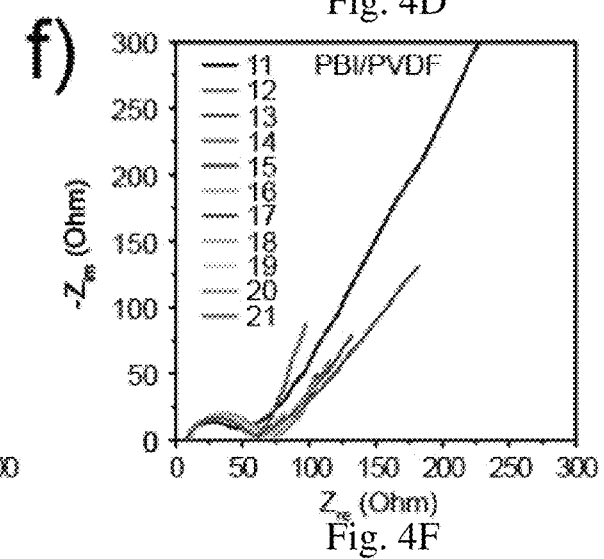

A much more complex evolution of impedance spectra was observed in the case of PBI, where a depressed semicircle at high frequencies and a long sloping line at low frequencies was initially observed at 100% SOC (see FIGS. 4C-4D). Upon discharge, a second semicircle in the middle frequency region began to emerge (points 2-6) and by 27% SOC (point 7) the middle frequency semicircle began to dominate the spectra with a sloping tail growing in the region between 40-80 mHz (points 7-9). Growth of a middle frequency semicircle has been previously attributed to the formation of a resistive $Li_2S$ (or $Li_2S_2$) film on the sulfur cathode, which impedes diffusion of counterions and polysulfides to the current collector. At the end of discharge (point 10) the semicircle in the middle frequency region and sloping line at low frequency are completely merged. This increase in impedance at 0% SOC may be due to mass-transport issues arising from the lower wettability of this cathode coupled with $Li_2S$ deposits blocking ion transport near the current collector. Immediately upon charging, the large semicircle in the middle and low frequency regions disappeared and the impedance of the cell decreased dramatically.

On the other hand, the PVDF/PBI composite binder cathode exhibited unique electrochemical behavior (see FIGS. 4E-4F), where the impedance decreased as the SOC approached 0% during discharge and the size of the semicircles remained small and nearly constant during the charge process, suggesting a unique activation had occurred in operando. Compared to the fully discharged PBI cathode, the PBI/PVDF composite binder cathode did not show any electrochemical behavior in the low frequency region that is associated with mass-transfer limitations. Instead, the EIS semicircles of the PBI/PVDF cathode were much smaller than those of the other two cathodes throughout the GITT, which is a sign of lower cell impedance overall and is in agreement with the enhanced rate capability during normal cell operation. Furthermore this lowest-impedance state appears to be sustainable at different SOCs.

Our findings suggest a re-examination may be in order for the ideal binder paradigm for composite electrodes. Whereas passive binders impart many useful functions as noted, redox-active binders offer a powerful new means to adapt the electrode's transport behaviors in operando and on demand.

Against conventional wisdom, we show that it is not necessary to configure the binder as a covalent high-polymer. Indeed, supramolecular approaches are also suitable; in fact, these may be preferred for electrode materials undergoing significant volume changes associated with conversion or alloying reactions, as is the case with sulfur and silicon electrodes. With this in mind, the networked architecture of the binder in the solid state and it's relationship to the electrode's active materials and embedded current collector become key to understanding cell performance—with high interface density contributing favorably to high rate-performance as observed here with the PBI/PVDF-derived sulfur cathodes.

We also suggest that we are only beginning to reveal the synergies between binder components, particularly with respect to their interactions with each other and with ions in the supporting electrolyte. For example, we hypothesize that the evolved, low, and sustained cell impedance that we observe only in the case of electrochemically-activated PBI/PVDF blends may arise from improved charge-separation of both $Li^+$ (which coordinates to reduced $Li_2$-PBI) and $TFSI^-$ (which coordinates to PVDF), which would improve their mobility within the composite and thus enable the high-rate performance. These foundational concepts in adaptive transport behaviors begin to map forward an exciting path in materials discovery at the interface of organic, polymer, supramolecular, and electrochemistry.

Instrumentation.

Contact angle measurements were performed using a Krüss EasyDrop. Scanning electron micrographs were taken using the in-lens detector of a Zeiss Gemini Ultra-55 outfitted with energy-dispersive X-ray spectroscopy (EDS, JEOL JSM-7500F) for elemental mapping. Thermogravimetric analysis (TGA) was used to determine the weight content of the S in the CTAB-modified S-GO nanocomposite with a heating rate of 10° C. $min^{-1}$ under $N_2$ atmosphere. Battery testing was performed on an Arbin BT2000 cycler. Electrochemical impedance spectroscopy was conducted with a BioLogic VMP3 potentiostat.

Materials.

PBI was synthesized according to a literature procedure. Lithium metal (99.98%) was purchased from Cyprus Foote Mineral. Sodium sulfide (Alfa Aesar, $Na_2S$, anhydrous), sulfur (Alfa Aesar, S, ~325 mesh, 99.5%) Graphene oxide ACS Material, cetyltrimethyl ammonium bromide (Sigma Aldrich, CTAB, $CH_3(CH_2)_{15}N(Br)(CH_3)_3$.) formic acid (Aqua Solutions).

Preparation of the CTAB-Modified S-GO Nanocomposite.

The CTAB-modified S-GO nanocomposite was prepared via a method as described in co-pending U.S. application Ser. No. 14/899,997. Briefly, 0.58 g of sodium sulfide powder was dissolved in 25 mL ultrapure water to form a $Na_2S$ solution. 0.72 g elemental sulfur powder was added to the $Na_2S$ solution and stirred with a magnetic stirrer at 60° C. until the solution became transparent orange color (a sodium polysulfide ($Na_2S_x$) solution). 18 mL of single layer graphene oxide dispersion (GO, 10 mg/mL) in water was diluted to form a GO suspension (180 mg of GO in 180 mL of ultrapure water). 2.5 mM of cetyltrimethyl ammonium bromide (CTAB, $CH_3(CH_2)_{15}N(Br)(CH_3)_3$) were added to the GO suspension and stirred for 2 h with a magnetic stirrer.

Then, the prepared Na$_2$S$_x$ solution was added to the GO-CTAB composite solution and stirred overnight. The as-prepared Na$_2$S$_x$-GO-CTAB composite solution was slowly added to 100 mL of 2 M formic acid (HCOOH) and stirred for 2 h to precipitate elemental S onto the GO. Finally, the CTAB-modified S-GO nano-composite was filtered and washed with acetone and ultrapure water several times to remove salts and impurities. The obtained powder sample was dried at 50° C. in a vacuum oven overnight. The dried powder sample was ground using mortar and pestle and heat-treated in a tube furnace at 155° C. for 12 h under Ar atmosphere.

Contact Angle Measurement.

Figure 11:
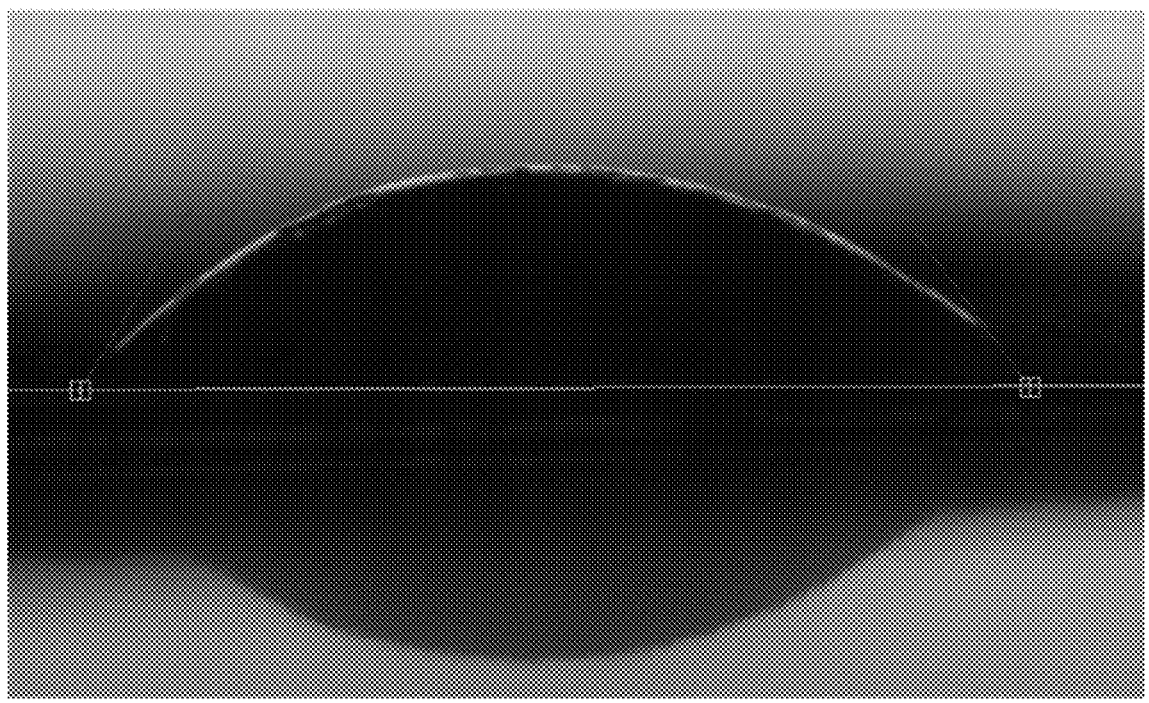
FIG. 11 illustrates a contact angle measurement for the PBI cathode with an electrolyte droplet (56°). PBI/PVDF and PVDF cathodes were instantly wetted.

Composite cathodes identical to those tested in coin cells were prepared with PBI, PVDF, and PBI/PVDF. The Easy-Drop instrument was placed in a glove bag and purged with N$_2$ for 1 h to prevent water uptake by the hygroscopic electrolyte from altering the measurement. PVDF and PBI/PVDF electrodes wet immediately by electrolyte and would not sustain a drop for contact angle measurement, whereas the PBI electrode showed a contact angle of 56° as is depicted in FIG. 11.

Li—S Cell Electrochemical Measurements.

The sulfur cathodes were prepared by mixing the S-GO nanocomposite, carbon black (Ketjenblack) with a binder (either the PBI, PVDF, or PBI/PVDF composite binder 1:1 by weight) at a weight ratio of 8:1:1 in N-methyl-2-pyrrolidone (NMP) solvent to form a slurry using magnetic stirrer. All Slurries were heated to 100° C. while stirring to completely dissolve the PBI binder into NMP and uniformly casted via a doctor blade on aluminum foil.

The cathode was first dried at room temperature for 24 h, and then dried in a vacuum oven at 50° C. for 24 h to fully eliminate any solvent residue. The average sulfur loading of the cathodes was 0.8-1.0 mg cm$^{-2}$. 1 M Lithium Bis (Trifluoromethanesulfonyl)Imide (LiTFSI) in N-methyl-N-butylpyrrolidinium bis(trifluoromethane sulfonyl)imide (PYR$_{14}$TFSI)/dioxolane (DOL)/Dimethoxyethane (DME) (2:1:1, v/v) containing 1 wt % LiNO$_3$ was prepared for the electrolyte. CR2325-type coin cells were fabricated with a lithium metal foil as counter/reference electrode and a porous polypropylene separator (2400, Celgard) in a glove box filled with Ar gas.

Cyclic voltammetry for the prepared cells was conducted using a potentiostat with a voltage range of 1.5 to 2.8 V for 5 cycles at a constant scan rate of 0.1 mV s$^{-1}$. The prepared cells were discharged and charged at 0.1 C rate using a procedure that consisted of galvanostatic discharge and charge pulses, each 45 min long, followed by 1 h of relaxation time, with open circuit status until the cell voltage reaches 1.5 V and the electrochemical impedance was measured from 10 mHz to 1 MHz using a potentiostat at the end of every relaxation step during discharge and charge. Galvanostatic cycling test of the coin cells was performed using a battery cycler between 1.5 and 2.8 V at 1.0 C and 0.5 C for discharge and charge, respectively. Rate capability tests were also performed at various discharge C rates from 0.1 C to 3.0 C and then back to 0.1 C.

All manipulations involving lithium metal were performed in an Ar-filled glove box with water and O$_2$ content below 2.0 ppm.

PBI Control Cell.

PBI and related rylene molecules are known organic cathode materials for Li-ion cells; therefore, a control cathode composed solely of supramolecular PBI binder and Ketjen black in a 1:1 weight ratio was subjected to CV and galvanostatic cycling (see FIGS. 12A and 12B). Even with PBI as 50% of the cathode mass a minimal capacity of 35 mAh/g (PBI) was measured, confirming that the capacity contribution of PBI to the PBI cathodes containing S-GO nanocomposite as active material is negligible.

Various embodiments of the invention describe a battery. In one embodiment, the battery comprises a cathode comprising a redox-active supramolecular polymer binder and a cetyltrimethyl ammonium bromide (CTAB) modified graphene oxide-sulfur (GO-S) nanocomposite, wherein GO further comprises a plurality of functional groups and S is bonded to carbon atoms. The battery may also comprise a separator, an anode, and an electrolyte.

The redox-active supramolecular polymer binder may comprises π-stacked perylene bisimide (PBI) molecules. The redox-active supramolecular polymer binder may comprise nanowires.

The cathode may further comprise a polyvinylidene difluoride (PVDF) polymer. Alternatively, the cathode may further comprise other types of binders including styrene butadiene rubber (SBR), polyethylene oxide (PEO), and carboxy methyl cellulose (CMC).

The cathode may further comprise Ketjenblack (KB) or carbon black (CB) or any other type of conductive additive.

The battery may include a separator comprising a porous polypropylene. The porous polypropylene may include a Celgard 3501, Celgard 2400, or other Celgard separators.

The battery may include an electrolyte comprising an ionic liquid-based electrolyte. The electrolyte may comprise a mixture of 1,3-dioxolane (DOL) and dimethoxyethane (DME) with lithium bis(trifluoromethylsulfonyl)imide (LiTFSI). The ionic liquid may comprise (n-methyl-(n-butyl) pyrrolidinium bis(trifluoromethanesulfonyl)imide (PYR$_{14}$TFSI). The electrolyte may comprise a lithium nitrate (LiNO$_3$) additive. The electrolyte may comprise PYR$_{14}$TFSI-LiTFSI-PEGDME. The electrolyte may comprise LiTFSI-PEGDME. The electrolyte may comprise Lithium Bis(Trifluoromethanesulfonyl)Imide (LiTFSI) in N-methyl-N-butylpyrrolidinium bis(trifluoromethane sulfonyl)imide (PYR$_{14}$TFSI)/dioxolane (DOL)/Dimethoxyethane (DME) (2:1:1, v/v) containing 1 wt % LiNO$_3$.

What is claimed is:

1. A composition of matter comprising:
   a redox-active supramolecular polymer binder comprising
      π-stacked perylene bisimide (PBI) molecules comprising a lithiated PBI molecule; and
   a cetyltrimethyl ammonium bromide (CTAB) modified graphene oxide-sulfur (GO-S) nanocomposite, wherein GO further comprises a plurality of functional groups and S is bonded to carbon atoms.

2. The composition of matter of claim 1, wherein the redox-active supramolecular polymer binder comprises nanowires.

3. The composition of matter of claim 2 further comprising a polyvinylidene difluoride (PVDF) polymer.

4. The composition of matter of claim 1, wherein the plurality of functional groups includes at least one functional group selected from the group consisting of an epoxy bridge, a hydroxyl group, a phenol group, and a carbonyl group.

5. An electrode comprising:
   a redox-active supramolecular polymer binder comprising
      π-stacked perylene bisimide (PBI) molecules comprising a lithiated PBI molecule; and
   a cetyltrimethyl ammonium bromide (CTAB) modified graphene oxide-sulfur (GO-S) nanocomposite, wherein GO further comprises a plurality of functional groups and S is bonded to carbon atoms.

6. The electrode of claim 5, wherein the redox-active supramolecular polymer binder comprises nanowires.

7. The electrode of claim 6 further comprising a polyvinylidene difluoride (PVDF) polymer.

8. The electrode of claim 7 further comprising Ketjenblack (KB) or carbon black (CB).

9. The electrode of claim 8, wherein the plurality of functional groups includes at least one functional group selected from the group consisting of an epoxy bridge, a hydroxyl group, a phenol group, and a carbonyl group.

10. The electrode of claim 9, wherein the electrode is a cathode.

11. A battery comprising:
   a cathode comprising:
      a redox-active supramolecular polymer binder comprising π-stacked perylene bisimide (PBI) molecules comprising a lithiated PBI molecule; and
      a cetyltrimethyl ammonium bromide (CTAB) modified graphene oxide-sulfur (GO-S) nanocomposite, wherein GO further comprises a plurality of functional groups and S is bonded to carbon atoms;
   a separator;
   an anode; and
   an electrolyte.

12. The battery of claim 11, wherein the redox-active supramolecular polymer binder comprises nanowires.

13. The battery of claim 12, wherein the cathode further comprising a polyvinylidene difluoride (PVDF) polymer.

14. The battery of claim 13, wherein the cathode further comprising Ketjenblack (KB) or carbon black (CB).

15. The battery of claim 11, wherein the plurality of functional groups includes at least one functional group selected from the group consisting of an epoxy bridge, a hydroxyl group, a phenol group, and a carbonyl group.

16. The battery of claim 11, wherein the separator comprises a porous polypropylene.

17. The battery of claim 11, wherein the porous polypropylene is a Celgard 3501 or a Celgard 2400.

18. The battery of claim 11, wherein the electrolyte comprises an ionic liquid-based electrolyte.

19. The battery of claim 18, wherein the electrolyte comprises a mixture of 1,3-dioxolane (DOL) and dimethoxyethane (DME) with lithium bis(trifluoromethylsulfonyl)imide (LiTFSI).

20. The battery of claim 19, wherein the ionic liquid comprises (n-methyl-(n-butyl) pyrrolidinium bis(trifluoromethanesulfonyl)imide (PYR14TFSI).

21. The battery of claim 20, wherein the electrolyte comprises a lithium nitrate (LiNO$_3$) additive.

22. The battery of claim 21, wherein the electrolyte comprises PYR$_{14}$TFSI-LiTFSI-PEGDME.

23. The battery of claim 22, wherein the electrolyte comprises LiTFSI-PEGDME.

24. The battery of claim 11, wherein the electrolyte comprises Lithium Bis(Trifluoromethanesulfonyl)Imide (LiTFSI) in N-methyl-N-butylpyrrolidinium bis(trifluoromethane sulfonyl)imide (PYR$_{14}$TFSI)/dioxolane (DOL)/Dimethoxyethane (DME) (2:1:1, v/v) containing 1 wt % LiNO$_3$.

25. The battery of claim 11, wherein the cathode further comprises an aluminum substrate.

26. The composition of matter of claim 1, wherein the PBI comprises the chemical structure:

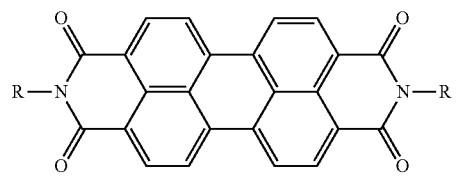

wherein R is

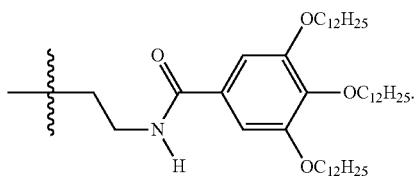

27. The electrode of claim 5, wherein the PBI comprises the chemical structure:

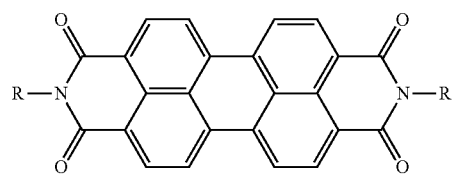

wherein R is

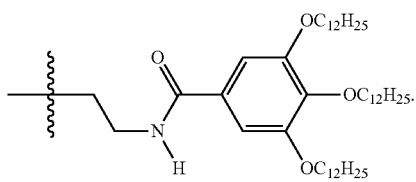

28. The battery of claim 11, wherein the PBI comprises the chemical structure:

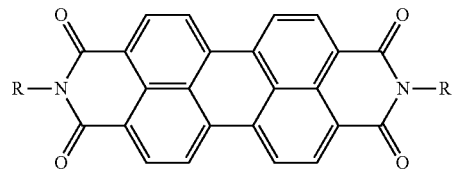

wherein R is

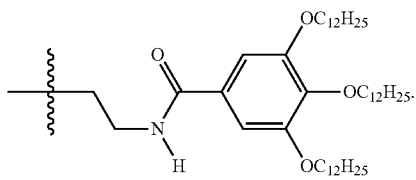

* * * * *